United States Patent [19]

Ogle

[11] 3,941,131

[45] Mar. 2, 1976

[54] DEVICE FOR ADMINISTRATION OF VISCOUS FLUIDS FOR THE URETHAL TRACT

[75] Inventor: Robert W. Ogle, Newport Beach, Calif.

[73] Assignee: IMS Limited, South El Monte, Calif.

[22] Filed: Aug. 8, 1973

[21] Appl. No.: 386,615

Related U.S. Application Data

[63] Continuation of Ser. No. 186,726, Oct. 5, 1971, abandoned.

[52] U.S. Cl. ............. 128/237; 128/220; 128/218 D
[51] Int. Cl.² ......................................... A61M 1/00
[58] Field of Search ............ 128/220, 218 D, 218 R, 128/272, 237, 239, 234, 261

[56] References Cited
UNITED STATES PATENTS

| | | | |
|---|---|---|---|
| 871,474 | 11/1907 | Buckner | 128/239 |
| 1,050,591 | 1/1913 | Ammons | 128/234 |
| 1,763,079 | 6/1930 | Zacsek | 128/239 |
| 1,817,003 | 8/1931 | Hein | 128/220 |
| 1,833,598 | 11/1931 | Smith | 128/237 |
| 1,848,711 | 3/1932 | Hall | 128/220 |
| 1,929,247 | 10/1933 | Hein | 128/220 X |
| 2,313,483 | 3/1943 | Smith | 128/218 D X |
| 2,568,346 | 9/1951 | Lockhart | 128/220 |
| 2,873,886 | 2/1959 | Miskel et al. | 128/261 UX R |
| 2,954,769 | 10/1960 | Callahan et al. | 128/272 |
| 3,171,412 | 3/1965 | Braun | 128/272 |
| 3,376,866 | 4/1968 | Ogle | 128/220 |
| 3,378,008 | 4/1968 | Ogle | 128/220 |
| 3,768,474 | 10/1973 | Burke et al. | 128/220 |

FOREIGN PATENTS OR APPLICATIONS 322,601  10/1968  Sweden .............................. 128/261

*Primary Examiner*—John D. Yasko
*Attorney, Agent, or Firm*—Wills, Green & Mueth

[57] ABSTRACT

An applicator useful for the administration of viscous or gel-type drugs to the human urethral tract. The applicator tip has an end through which the medicinal gel is expelled. Adjacent the end, is a cylindrical portion. Both the end and the cylindrical portions are of such size as to be receivable in the urethral tract. Above the cylindrical portion is a tapered zone which extends to the barrel and has its largest external diameter at the barrel. This tapered portion is only partially receivable in the urethral tract so as to seal the urethral tract during injection of the drugs.

9 Claims, 10 Drawing Figures

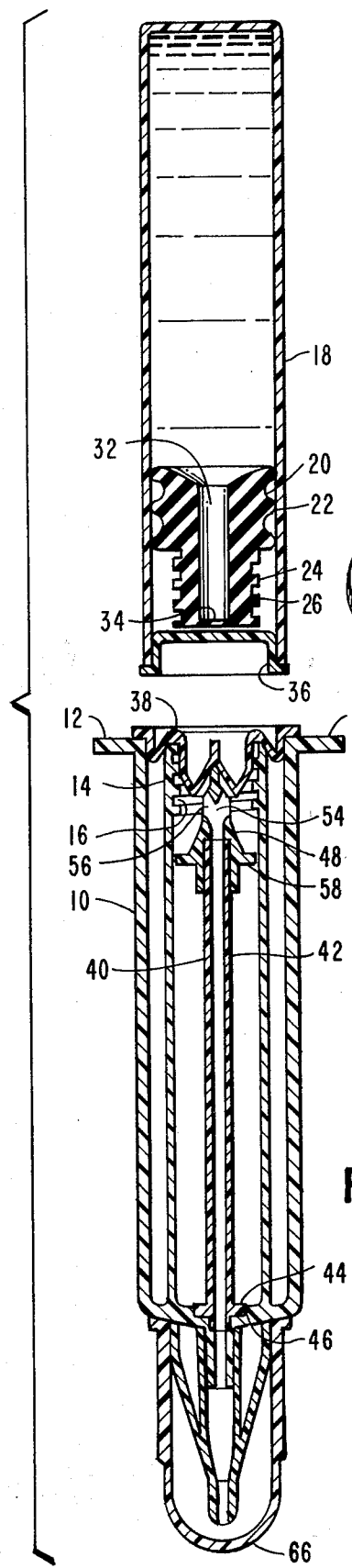
FIG.—1
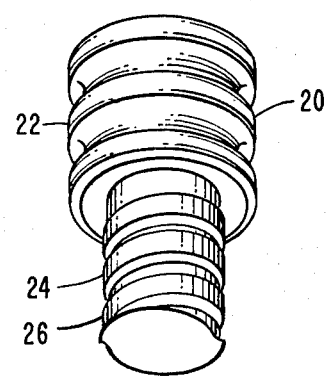
FIG.—4
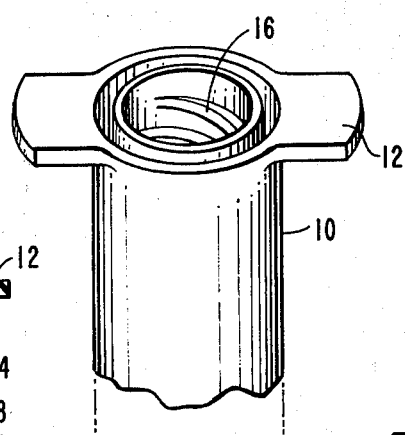
FIG.—5
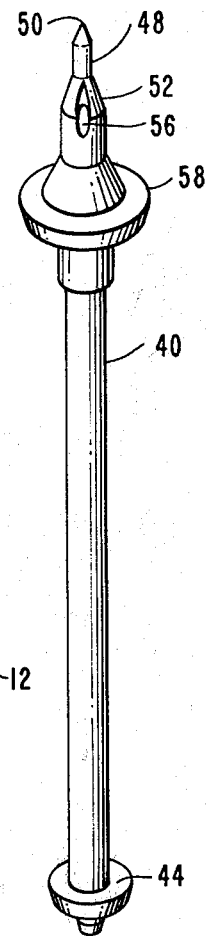
FIG.—3
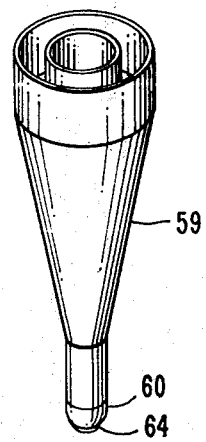
FIG.—2

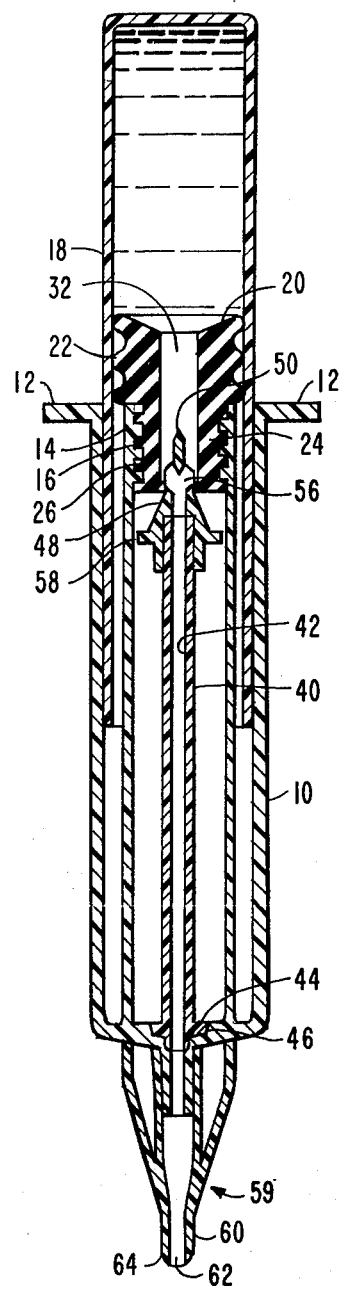
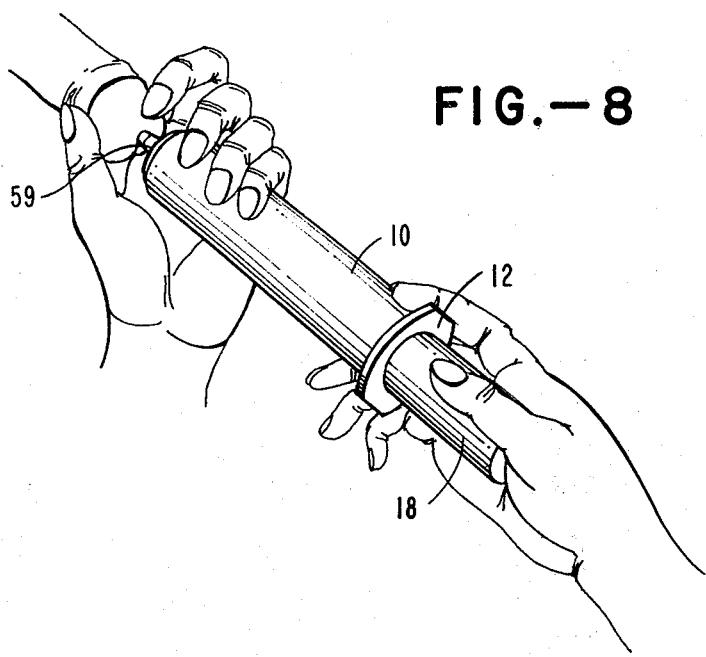
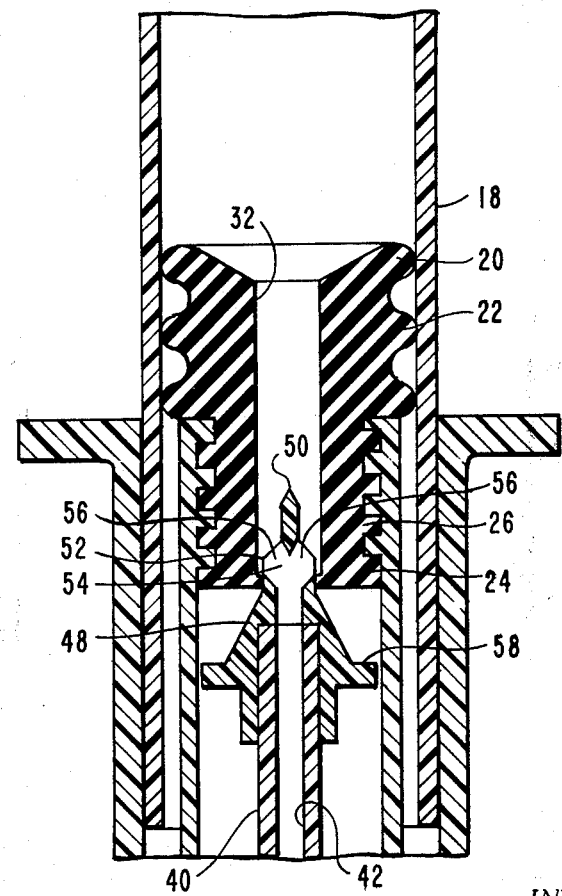
FIG.–6
FIG.–7
FIG.–8
INVENTOR.
ROBERT W. OGLE
BY
Finkelstein + Mueth
ATTORNEYS U.S. Patent  March 2, 1976  Sheet 3 of 3  3,941,131
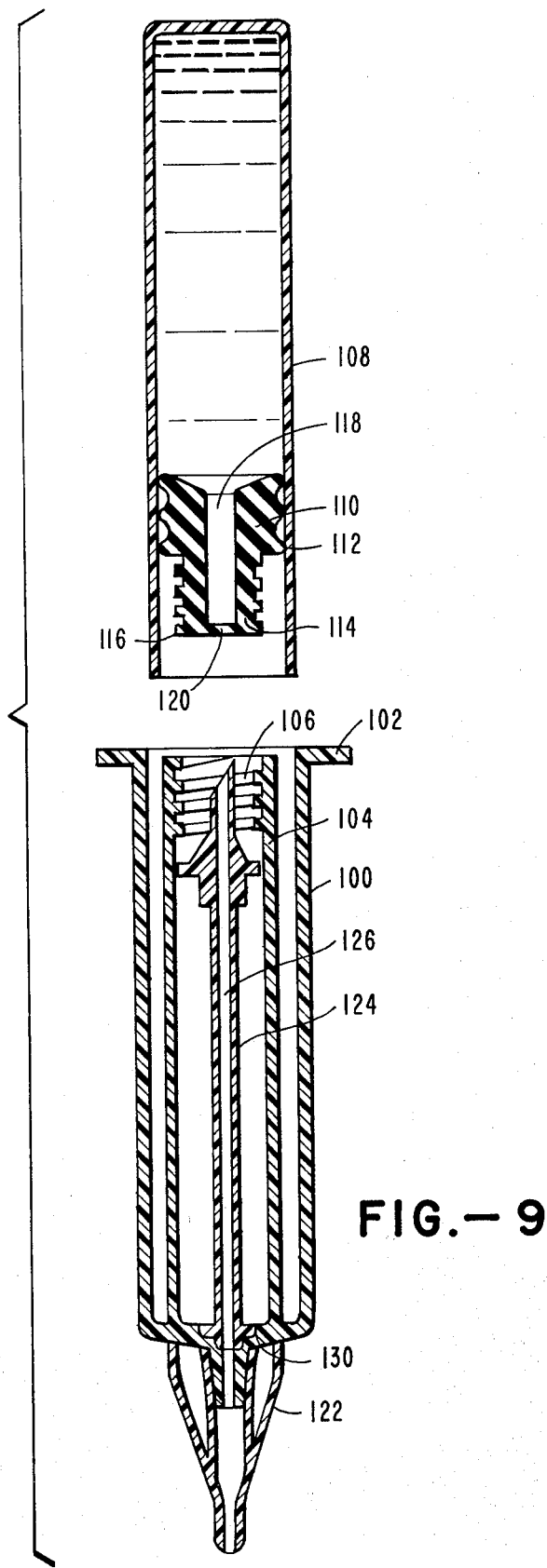
FIG.—9
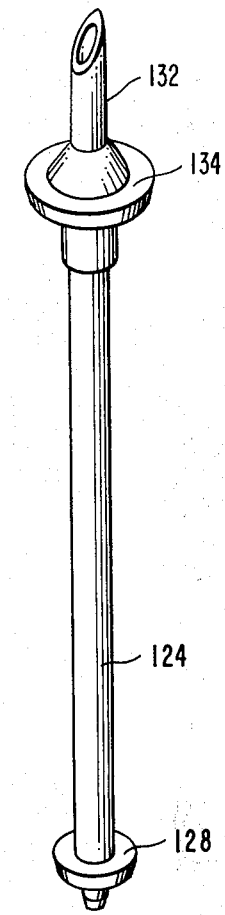
FIG.—10
INVENTOR.
ROBERT W. OGLE
BY
Finkelstein & Mueth
ATTORNEYS

DEVICE FOR ADMINISTRATION OF VISCOUS FLUIDS FOR THE URETHAL TRACT

This is a continuation of application Ser. No. 186,726, filed on Oct 5, 1971, now abandoned.

BACKGROUND OF THE INVENTION

Various medicaments are administered to the urethral tract. One of the most common is the administration of a topical anesthetic such as lidocaine hydrochloride which is used in the form of a viscous fluid having a carboxymethyl cellulose carrier. Presently, this viscous fluid is supplied in a malleable metal, roll-up tube which resembles a toothpaste tube. In use, a urethral tip is attached to the open end of the tube, and a key is attached to the closed end of the tube. By rotation of the key, the tube is rolled up, discharging the contents of the tube through the tip. This device is very awkward in use. In the case of administration to males, it is virtually impossible for one person to administer the medication since one hand is needed to hold the tube, a second is required to turn the key to roll-up the tube, and a third being necessary to maintain the urethal tip within the end of the penis.

There has been a long-standing need for a device capable of use by a single physician or nurse to administer medicaments to the urethral tract. It is believed that the present invention meets this need by providing a device which is operable with one hand, freeing the other for maintaining the urethral tip in the proper position.

SUMMARY OF THE INVENTION

Briefly, this invention relates to a novel device especially useful for the administration of viscous fluids to the human urethral tract comprising: a barrel having an open end and a closed end, a thrust portion within said barrel and terminating in proximity to the open end of said barrel, projecting upward within said thrust portion, a fluid passage member terminating within said thrust portion, said fluid passage having a central bore, puncturing means associated with the upper end of said fluid passage, a flange on said fluid passage member adapted to limit the lateral movement of said fluid passage member with relation to said thrust portion to maintain an essentially concentric relationship therebetween, a urethral tip extending from said barrel and communicating with said central bore, a vial having an open end and a closed end, a resilient reciprocating stopper sealing on the walls of said vial, said stopper having a center hole therein bridged by an imperforate diaphragm, said diaphragm being adapted to be punctured by said puncturing means.

It is an object of this invention to provide a novel device for the administration of medication to the urethral tract.

More particularly, it is an object of this invention to provide a novel device which allows one person to administer medication to the urethral tract.

It is also an object of this invention to provide a device which eliminates the need for malleable tubes and other metal parts.

A further object of this invention is to provide for the administration of viscous medication with a minimum of time and manual effort.

These and other objects and advantages of this invention will be apparent from the detailed description which follows considered in conjunction with the accompanying drawings.

DESCRIPTION OF THE PREFERRED EMBODIMENTS

Turning to the drawings:

FIG. 1 is a sectional view of the preferred embodiment of my invention in the disassembled state.

FIG. 2 is a perspective view of the urethral tip of this invention.

FIG. 3 is a perspective view of the fluid passage member of this invention.

FIG. 4 is a perspective view of the stopper used in this invention.

FIG. 5 is a perspective view of the end of the thrust portion within the barrel.

FIG. 6 is a sectional view of the device of FIG. 1 in the assembled or operating position.

FIG. 7 is an enlarged view of the stopper and end of the thrust portion when the device is in the assembled or operating position.

FIG. 8 shows the use of the device in the administration of a drug to the penis.

FIG. 9 illustrates another embodiment of this invention.

FIG. 10 is a perspective view of the fluid passage member of the device of FIG. 9.

Turning to the drawings in detail, the device illustrated includes barrel 10, flanges 12, and thrust portion 14. The thrust portion 14 is provided with internal or female threads 16 at its open end.

The vial 18 normally has straight walls and a resilient reciprocating stopper 20 within its open end. The stopper 20 has a plurality of rings 22 which seal on the inside wall of the vial 18. The stopper 20 also has a threaded projection 24. The male threads 26 on projection 24 are adapted to be made up with threads 16. The stopper 20 has a central bore 32 which is bridged prior to use by diaphragm 34 to form a flat smooth end.

The caps 36 and 38 which form an asceptic seal on the vial and barrel, respectively, prior to use are held in place by an interference or snap-fit. At the time of use, these caps are removed and discarded. The fluid passage member 40 has an enlarged center bore 42 which allows for the ready passage of viscous or thixotropic materials therethrough. The flange 44 on the fluid passage member 40 is received and held in recess 46 in the bottom of barrel 10. The fluid passage member 40 may be held in recess 46 by fusion, such as is produced by spin welding, or by glue or cement. The fluid passage member 40 is provided at its free end with tip 48 which comprises at its upper end solid puncturing point 50 having a generally circular cross-section, which is a zone 52 of generally larger diameter than said point, the interior 54 of said zone 52 communicating with central bore 42, said zone 52 having one or more orifices or openings 56 therein to provide fluid communication between central bore 42 and the exterior of zone 52. The external diameter of zone 52 in proximity to the orifices 56 is less than the inside diameter of the central bore 32 of stopper 20. The interior 54 of the zone 52 is preferably adapted to receive the end of fluid passage member 40 with a snug or interference fit. The inside diameter of zone 52 above the end of fluid passage member 40 preferably has the same as the diameter of central bore 42 to provide a fluid passage of substantially uniform cross-sectional area.

The flange 58 on the tip 48 acts as a centralizer, and prevents any substantial lateral movement of the tip 48 and fluid passage member 40 within thrust portion 14. Flange 58 thus assures that the tip 48 and its orifices 56 are within central bore 32, to provide proper fluid communication.

The urethral tip 59 extends from the closed end of barrel 10. The central or axial opening in tip 59 is in alignment with center bore 42. The end of tip 59 is generally cylindrical in cross-section, as shown at 60, and has a smooth external surface. The opening 62 in the end of tip 59 meets the cylindrical portion 60 in a rounded-off portion 64.

The cover 66 is received with a snap fit on the exterior of tip 59 to form an asceptic seal. The cover 66 is, of course, removed just prior to use.

The tip 59 can be spun welded, glued, or otherwise formed or joined with the barrel 10.

In operation, the device is made up to establish fluid communicating between the vial 18 and the fluid passage member 40 as shown in FIGS. 6 and 7 by the making up of threads 16 and 26. The tip 59 is then inserted in the urethral tract as shown in FIG. 8. The device may be held in place with one hand by grasping, for example, the lower end of barrel 10 and the end of the penis. Injection of the contents of vial 18 is then carried out within the other hand by applying a squeezing force between the end of vial 18 and flanges 12 until the stopper 20 has bottomed out in vial 18.

The invention is particularly adapted to the administration of thick viscous materials such as lidocaine hydrochloride in a carboxymethyl cellulose carrier. The inside diameter of central bore 42 is considerably larger than that of a conventional large gage cannula. The size of central bore 42 permits the discharge therethrough of viscous materials with a minimum of time and manual effort on the part of the physician or nurse. The invention is, however, not limited to the administration of thick viscous materials, nor is it limited to use in the urethral tract.

Turning to the embodiment of FIGS. 9 and 10, the barrel 100, flanges 102, thrust portion 104 and threads 106 are as previously described. Likewise, vial 108, stopper 110, sealing rings 112, projection 114, threads 116, central bore 118, diaphragm 120 and tip 122 remain unchanged. The fluid passage member 124 is provided with an enlarge central bore 126 which allows the ready passage of viscous material therethrough. The flange 128 is received in recess 130 in the bottom of barrel 100. The external diameter of the free end 132 of fluid passage member 124 may be smaller, equal to, or even slightly larger than the inside diameter of central bore 118. The centralizing disk or flange 134 functions as previously described.

The materials of construction are normally plastic except for the glass vial 18 and the rubber stopper 20.

Having fully described the invention, it is intended that it be limited only by the lawful scope of the appended claims.

I claim:

1. A novel device for the administration of viscous fluids comprising:

a barrel having an open end and a closed end, a thrust portion within said barrel and terminating in proximity to the open end of said barrel, projecting upward within said thrust portion a fluid passage member terminating within said thrust portion, said fluid passage having a central bore of a diameter sufficient to readily allow the passage of thick viscous fluid therethrough, a flange on said fluid passage member adapted to limit the lateral movement of said fluid passage member with relation to said thrust portion to maintain an essentially concentric relationship therebetween, the largest diameter of said flange being less than the internal diameter of said thrust portion, a tip carried on said fluid passage above said flange and comprising at its upper end a solid puncturing point below which is a zone of generally larger diameter than said point, the interior of said zone communicating with said central bore, said zone having one or more orifices therein to provide fluid communication between the central bore and the exterior of said zone, an elongated urethral tip having a hollow internal central bore extending from said barrel which communicates with said central bore of said fluid passage, the bore of said tip being at least equal in inside diameter to the inside diameter of said fluid passage, said tip having a smooth rounded end and a hole in said rounded end which serves as an outlet for said central bore, immediately above said end a cylindrical portion, said end and cylindrical portion being adapted to be received within the urethral tract, above said cylindrical portion, an externally tapered portion extending toward said barrel and having its largest external diameter at said barrel, the exterior of said tapered portion sealing the urethral tract during injection, a vial having an open end and a closed end, said vial containing a thick viscous fluid, a resilient reciprocating stopper sealing on the walls of said vial, said stopper having a center hole therein bridged by an imperforate diaphragm, said diaphragm being adapted to be punctured by said puncturing point, and the center hole of said stopper being larger in internal diameter than the exterior of said zone in proximity to said orifices, means on said resilient reciprocating stopper and said thrust portion whereby said stopper and thrust portion are interlocked and said stopper can be reciprocated whithin said vial by pushing or pulling on said vial.

2. A novel device for the administration of viscous fluids comprising:

a barrel having a open and a closed end, a thrust portion within said barrel and terminating in proximity to the open end of said barrel, projecting upward within said thrust portion, a fluid passage member terminating within said thrust portion, said fluid passage having a central bore of a diameter sufficient to readily allow the passage of thick viscous fluid therethrough, a flange on said fluid passage member adapted to limit the lateral movement of said fluid passage member with relation to said thrust portion to maintain an essentially concentric relationship therebetween, the largest diameter of said flange being less than the largest internal diameter of said thrust portion, a tip carried on said fluid passage above said flange and comprising at its upper end a solid puncturing point below which is a zone of generally larger diameter than said point, the interior of said zone communicating between the central bore, said zone having one or more orifices therein to provide fluid communication between the central bore and the exterior of said zone, an elongated smooth urethral tip having a hollow internal central bore extending from said barrel which communicates with said central bore of said fluid passage, said tip having a smooth rounded end and a hole in said rounded end which serves as an outlet for said central bore, immediately above said end a cylindrical portion, said end and cylindrical portion being adapted to be received within the urethral tract, above said cylindrical portion, an externally tapered portion extending toward said barrel and having its largest external diameter at said barrel, the exterior of said tapered portion sealing said urethral tract during injection, a vial having an open end and a closed end, said vial containing a thick viscous fluid, a resilient reciprocating stopper sealing on the walls of said vial, said stopper having a center hole therein bridged by an imperforate diaphragm at the outer end of said stopper, said diaphragm being adapted to be punctured by said puncturing point, and the center hole of said stopper being larger in internal diameter than the exterior of said zone in proximity to said orifices, means on said resilient reciprocating stopper and said thrust portion whereby said stopper and thrust portion are interlocked and said stopper can be reciprocated within said vial by pushing or pulling on said vial.

3. A novel device for the administration of viscous fluids comprising:

a barrel having an open end and a closed end, a thrust portion within said barrel and terminating in the proximity to the open end of said barrel, projecting upward within said thrust portion, a fluid passage member terminating within said thrust portion, said fluid passage having a central bore of a diameter sufficient to readily allow the passage of thick viscous fluid therethrough, a flange on said fluid passage member adapted to limit the lateral movement of said fluid passage member with relation to said thrust portion to maintain an essentially concentric relationship therebetween, the largest diameter of said flange being less than the largest internal diameter of said thrust portion, a tip carried on said fluid passage above said flange and comprising at its upper end a solid puncturing point below which is a zone of generally larger diameter than said point, the interior of said zone communicating with said central bore, said zone having one or more orifices therein to provide fluid communication between the central bore and the exterior of said zone, an elongated smooth urethral tip having a hollow internal central bore extending from said barrel which communicates with said central bore of said fluid passage, said tip having a smooth rounded end and a hole in said rounded end which serves as an outlet for said central bore, immediately above said end a cylindrical portion, said end and cylindrical portion being adapted to be received within the urethral tract, above said cylindrical portion, an externally tapered portion extending toward said barrel and having its largest external diameter at said barrel, the exterior of said tapered portion sealing the urethral tract during injection, a vial having an open end and a closed end, a viscous reagent within said vial, a resilient reciprocating stopper sealing on the walls of said vial, said stopper having a center hole therein bridged by an imperforate diaphragm, said diaphragm being adapted to be punctured by said puncturing point, and the center hole of said stopper being larger in internal diameter than the exterior of said zone in proximity to said orifices, means on said resilient reciprocating stopper and said thrust portion whereby said stopper and thrust portion are interlocked and said stopper can be reciprocated within said vial by pushing or pulling on said vial.

4. A novel device for the administration of viscous fluids comprising:

a barrel having an open end and a closed end, a thrust portion within said barrel and terminating in proximity to the open end of said barrel, said thrust portion having a free end which is internally threaded, projecting upward within said thrust portion, a fluid passage member terminating within said thrust portion, said fluid passage having a central bore of a diameter sufficient to readily allow the passage of thick viscous fluid therethrough, a flange on said fluid passage member adapted to limit the lateral movement of said fluid passage member with relation to said thrust portion to maintain an essentially concentric relationship therebetween, the largest diameter of said flange being less than the largest internal diameter of said thrust portion, a tip carried on said fluid passage above said flange and comprising at its upper end a solid puncturing point below which is a zone of generally larger diameter than said point, the interior of said zone communicating with said central bore, said zone having one or more orifices therein to provide fluid communication between the central bore and the exterior of said zone, an elongated smooth urethral tip having a hollow internal central bore extending from said barrel which communicates with said central bore of said fluid passage, said tip having a smooth rounded end and a hole in said rounded end which serves as an outlet for said central bore, immediately above said end a cylindrical portion, said end and cylindrical portion being adapted to be received within the urethral tract, above said cylindrical portion, an externally tapered portion extending toward said barrel and having its largest external diameter at said barrel, the exterior of said tapered portion sealing said urethral tract during injection, a vial having an open end and a closed end, said vial containing a thick viscous fluid, a resilient reciprocating stopper sealing on the walls of said vial, said stopper having an externally threaded projection thereon made up with internal threads on the end of said thrust portion whereby said stopper can be reciprocated within said vial by pushing or pulling on said vial, said stopper and projection having a center hole therein bridged by an imperforate diaphragm, said diaphragm being adapted to be punctured by said puncturing point when said threads are made up, and the center hole of said stopper being larger in internal diameter than the exterior of said zone in proximity to said orifices.

5. A novel device for the administration of viscous fluids comprising:

a barrel having an open end and a closed end, a thrust portion within said barrel and terminating in proximity to the open end of said barrel, projecting upward within said thrust portion a fluid passage member terminating within said thrust portion, said fluid passage having a central bore of a diameter sufficient to readily allow the passage of thick viscous fluid therethrough, a flange on said fluid passage member adapted to limit the lateral movement of said fluid passage member with relation to said thrust portion to maintain an essentially concentric relationship therebetween, the largest diameter of said flange being less than the largest internal diameter of said thrust portion, a tip carried on said fluid passage above said flange and comprising at its upper end a solid puncturing point below which is a zone of generally larger diameter than said point, the interior of said zone communicating with said central bore, said zone having one or more orifices therein to provide fluid communication between the central bore and the exterior of said zone, an elongated smooth urethral tip having a hollow internal central bore extending from said barrel which communicates with said central bore of said fluid passage, said tip having a smooth rounded end and a hole in said rounded end which serves as an outlet for said central bore, immediately above said end a cylindrical portion, said end and cylindrical portion being adapted to be received within the urethral tract, above said cylindrical portion, an externally tapered portion extending toward said barrel and having its largest external diameter at said barrel, the exterior of said tapered portion sealing said urethral tract during injection, a vial having an open end and a closed end, said vial containing a thick viscous fluid, a resilient reciprocating stopper sealing on the walls of said vial, said stopper having a center hole therein bridged by an imperforate diaphragm, said diaphragm being adapted to be punctured by said puncturing point, and the center hole of said stopper being larger in internal diameter than the exterior of said zone in proximity to said orifices, means on said resilient reciprocating stopper and said thrust portion whereby said stopper and thrust portion are interlocked and said stopper can be reciprocated within said vial by pushing or pulling on said vial.

6. A novel device for the administration of viscous fluids comprising:

a barrel having an open end and a closed end, a thrust portion within said barrel and terminating in proximity to the open end of said barrel, projecting upward within said thrust portion, a fluid passage member terminating within said thrust portion, said fluid passage having a central bore of a diameter sufficient to readily allow the passage of thick viscous fluid therethrough, a flange on said fluid passage member adapted to limit the lateral movement of said fluid passage member with relation to said thrust portion to maintain an essentially concentric relationship therebetween, the largest diameter of said flange being less than the largest internal diameter of said thrust portion, a tip carried on said fluid passage above said flange and comprising at its upper end a solid puncturing point below which is a zone of generally large diameter than said point, the interior of said zone having one or more orifices therein to provide fluid communication between the central bore and the exterior of said zone, an elongated smooth urethral tip having a hollow internal central bore extending from said barrel which communicates with said central bore of said fluid passage, said tip having a smooth rounded end and a hole in said rounded end which serves as an outlet for said central bore, immediately above said end a cylindrical portion, said end and cylindrical portion being adapted to be received within the urethral tract, above said cylindrical portion, an externally tapered portion extending toward said barrel and having its largest external diameter at said barrel, the exterior of said tapered portion sealing said urethral tract during injection, a cylindrical shell vial having an open end and a closed end, said vial containing a thick viscous fluid, a resilient reciprocating stopper sealing on the walls of said vial, said stopper having a center hole therein bridged by an imperforate diaphragm at the outer end of said stopper, said diaphragm being adapted to be punctured by said puncturing point, and the center hole of said stopper being larger in internal diameter than the exterior of said zone in proximity to said orifices, means on said resilient reciprocating stopper and said thrust portion whereby said stopper and thrust portion are interlocked and said stopper can be reciprocated within said vial by pushing or pulling on said vial.

7. A novel device for the administration of viscous fluids comprising:

a barrel having an open end and a closed end, a thrust portion within said barrel and terminating in proximity to the open end of said barrel, projecting upward within said thrust portion, a fluid passage member terminating within said thrust portion, said fluid passage having a central bore of a diameter sufficient to readily allow the passage of thick viscous fluid therethrough, a flange on said fluid passage member adapted to limit the lateral movement of said fluid passage member with relation to said thrust portion to maintain an essentially concentric relationship therebetween, the largest diameter of said flange being less than the largest internal diameter of said thrust portion, a tip carried on said fluid passage above said flange and comprising at its upper end a solid puncturing point below which is a zone of generally larger diameter than said point, the interior of said zone communicating with said central bore, said zone having one or more orifices therein to provide fluid communication between the central bore and the exterior of said zone, an elongated smooth urethral tip having a hollow internal central bore extending from said barrel which communicates with said central bore of said fluid passage, said tip having a smooth rounded end and a hole in said rounded end end which serves as an outlet for said central bore, immediately above said end a cylindrical portion, said end and said cylindrical portion being adapted to be received within the urethral tract, above said cylindrical portion, an externally tapered portion extending toward said barrel and having its largest external diameter at said barrel, the exterior of said tapered portion sealing said urethral tract during injection, a cylindrical shell vial having an open end and a closed end, a viscous reagent within said vial, a resilient reciprocating stopper sealing on the walls of said vial, said stopper having a center hole therein bridged by an imperforate diaphragm at the outer end of said stopper, said diaphragm being adapted to be punctured by said puncturing point, and the center hole of said stopper being larger in internal diameter than the exterior of said zone in proximity to said orifices, means on said resilient reciprocating stopper and said thrust portion whereby said stopper and thrust portion are interlocked and said stopper can be reciprocated within said vial by pushing or pulling on said vial.

8. A novel device for the administration of viscous fluids comprising:

a barrel having an open end and a closed end, a thurst portion within said barrel and terminating in proximity to the open end of said barrel, said thrust portion having a free end which is internally threaded, projecting upward within said thrust portion a fluid passage member terminating within said thrust portion, said fluid passage having a central bore of a diameter sufficient to readily allow the passage of thick viscous fluid therethrough, a flange on said fluid passage member adapted to limit the lateral movement of said fluid passage member with relation to said thrust portion to maintain an essentially concentric relationship therebetween, the largest diameter of said flange being less than the largest internal diameter of said thrust portion, a tip carried on said fluid passage above said flanges and comprising at its upper end a solid puncturing point below which is a zone of generally larger diameter than said point, the interior of said zone communicating with said central bore, said zone having one or more orifices therein to provide fluid communication between the central bore and the exterior of said one, an elongated smooth urethral tip having a hollow internal central bore extending from said barrel which communicates with said central bore of said fluid passage, said tip having a smooth rounded end and a hole in said rounded end which serves as an outlet for said central bore, immediately above said end a cylindrical portion, said end and cylindrical portion being adapted to be received within the urethral tract, above said cylindrical portion, an externally tapered portion extending toward said barrel and havings its largest external diameter at said barrel, the exterior of said tapered portion sealing the urethral tract during injection, a cylindrical shell vial having an open end and a closed end, said vial containing a thick viscous fluid, a resilient reciprocating stopper sealing on the walls of said vial, said stopper having an externally threaded projection thereon made up with internal threads on the end of said thrust portion whereby said stopper can be reciprocated within said vial by pushing or pulling on said vial, said stopper and projection having a center hole therein bridged by an imperforate diaphragm, at the outer end of said stopper, said diaphragm being adapted to be punctured by said puncturing point when said threads are made up, and the center hole of said stopper being larger in internal diameter than the exterior of said zone in proximity to said orifices.

9. A novel device for the administration of viscous fluids comprising:

a barrel having an open end and a closed end, a thrust portion within said barrel and terminating in proximity to the open end of said barrel, said thrust portion having a free end which is internally threaded, projecting upward within said thrust portion, a fluid passage member terminating within said thrust portion, said fluid passage having a central bore of a diameter suffcient to readily allow the passage of thick viscous fluid therethrough, a flange on said fluid passage member adapted to limit the lateral movement of said fluid passage member with relation to said thrust portion to maintain an essentially concentric relationship therebetween, the largest diameter of said flange being less than the largest internal diameter of said thrust portion, a tip carried on said fluid passage above said flange and comprising at its upper end a solid puncturing point below which is a zone of generally larger diameter than said point, the interior of said zone communicating with said central bore, said zone having one or more orifices therein to provide fluid communication between the central bore and the exterior of said zone, an elongated smooth urethral tip having a hollow internal central bore extending from said barrel which communicates with said central bore of said fluid passage, said tip having a smooth rounded end and a hole in said rounded end which serves as an outlet for said central bore, immediatedly above said end a cylindrical portion, said end and cylindrical portion being adapted to be received within the urethral tract, above said cylindrical portion, an externally tapered portion extending toward said barrel and having its largest external portion at said barrel, said exterior of said tapered portion sealing said urethral tract during injection, a cylindrical shell vial having an open and a closed end, a viscous reagent within said vial, a resilient reciprocating stopper sealing on the walls of said vial, said stopper having an externally threaded projection thereon made up with internal threads on the end of said thrust portion whereby said stopper can be reciprocated within said vial by pushing or pulling on said vial, said stopper and projection having a center hole therein bridged by an imperforate diaphragm, said diaphragm being adapted to be punctured by said puncturing point when said threads are made up, and the center hole of said stopper being larger in internal diameter than the exterior of said zone in proximity to said orifices.

* * * * *